US006461611B1

(12) United States Patent
Bar-Shavit

(10) Patent No.: US 6,461,611 B1
(45) Date of Patent: Oct. 8, 2002

(54) AGENTS FOR THE PREVENTION OF DAMAGES CAUSED BY STRESS CONDITIONS

(75) Inventor: Rachel Bar-Shavit, Jerusalem (IL)

(73) Assignee: Hadasit Medical Research Services & Development Limited, Jerusalem (IL)

( * ) Notice: Subject to any disclaimer, the term of this patent is extended or adjusted under 35 U.S.C. 154(b) by 0 days.

(21) Appl. No.: 09/600,031

(22) PCT Filed: Feb. 16, 1999

(86) PCT No.: PCT/IL99/00095

§ 371 (c)(1),
(2), (4) Date: Jul. 20, 2000

(87) PCT Pub. No.: WO99/42483

PCT Pub. Date: Aug. 26, 1999

(30) Foreign Application Priority Data

Feb. 18, 1998 (IL) .................................................. 123349

(51) Int. Cl.[7] ............................ A61K 38/48; C07K 7/00
(52) U.S. Cl. .................... 424/94.64; 530/327; 530/328; 530/329; 530/330
(58) Field of Search ....................... 424/94.64; 530/327, 530/328, 329, 330

(56) References Cited

U.S. PATENT DOCUMENTS 5,256,766 A  * 10/1993 Couglhlin

FOREIGN PATENT DOCUMENTS

EP         WO 92/14750         9/1992

OTHER PUBLICATIONS

Johannes Ruel et al., A Novel Effect of Fluid Shear Stress: Down–regulation of Human Thrombin Receptor mRNA and Promoter Activity in Human Aortic Smooth Muscle Cells, XP–002110121 (Abstract).
Shaun R. Coughlin et al., "Characterization of a Functional Thrombin Receptor," *The American Society for Clinical Investigation, Inc.*, vol. 809, pp. 351–355, Feb. 1992.
Rosemary J. Santulli et al., "Evidence for the Presence of a Protease–activated Receptor Distinct from the Thrombin Receptor in Human Keratinocytes," *Proc. Natl. Acad. Sci., USA*, vol. 92, 1995.
Peter Grabham et al., "Thrombin Receptor Activation Stimulates Astrocyte Proliferation and Reversal of Stellation by Distinct Pathways: Involvement of Tyrosine Phoshphorylation," *Journal of Neurochemistry*, vol. 64, pp. 583–591, 1995.
Christopher C. Glembotski et al., "Myocardial α–Thrombin Receptor Activation Induces Hypertrophy and Increases Atrial Natriuretic Factor Gene Expression," *The Journal of Biological Chemistry*, vol. 268, No. 27,pp. 20616–20652, Sep. 1993.

Thien–Khai H. Vu et al., "Molecular Cloning of a Function Thrombin Receptor Reveals a Novel Proteolytic Mechanism of Receptor Activation," *Cell Press*, vol. 64, pp. 1057–1068, Mar. 1991.
Rachel Bar–Shavit et al., "Binding of Thrombin to Subendothelial Extracellular Matrix: Protection and Expression of Functional Properties," *The American Society for Clinical Investigation, Inc.*, vol. 84, pp. 1096–1104, Oct. 1989.
Dorit Shweiki et al., "Vascular Endothelial Growth Factor Induced by Hypoxia May Mediate Hypoxia–initiated Angiogenesis," *Letters to Nature*, vol. 359, pp. 843–845, Oct. 1992.
Valentina A. Schmidt et al., "Genomic Cloning and Characterization of the Human Thrombin Receptor Gene , Structural Similarity to the Proteinase Activated Receptor–2 Gene," *The Journal of Biological Chemistry*, vol. 271, No. 16, pp. 9307–9312, Apr. 1996.
Sverker Nystedt et al., "Molecular Cloning and Functional Expression of the Gene Encoding the Human Proteinase–activated Receptor 2," *Eur. J. Biochem*, vol. 232, pp. 84–89, 1995.
Shaun R. Coughlin, "Protease–activated Receptors Start a Family," *Proc., Natl., Acad., Sci., USA*, vol. 91, pp. 9200–9202, Sep. 1994.
Sverker Nystedt et al., "Molecular Cloning of a Potential Proteinase Activated Receptor," *Proc., Natl., Acad., Sci., USA*, vol. 91, pp. 9208–9212, Sep. 1994.
T. Sabo et al., "Structure–activity Studies of the Thrombin Receptor Activating Peptide," *Biochemical and Biophysical Research Communication*, 188, No. 2, Oct. 1992.
Karla S. Rugh et al., "Ischaemia Induced Development of Functional Coronary Collateral Circulation in Ponies," *Cardiovascular Research*, 21, pp. 730–736, 1987.
Douglas Kondziolka et al., "Symptomatic Arterial Luminal Narrowing Presenting Months After Subarachnoid Hemorrhage and Aneurysm Clipping," *J. Neurosurg*, vol. 69, pp. 494–499, Oct. 1988.
Wolfgang Schaper et al., "DNA Synthesis and Mitoses in Coronary Collateral Vessels of the Dog," *Circulation Research*, vol. XXVIII, pp. 671–679, Jun. 1971.

(List continued on next page.)

*Primary Examiner*—Christopher R. Tate
*Assistant Examiner*—Randall Winston
(74) *Attorney, Agent, or Firm*—Oliff & Berridge, PLC

(57) ABSTRACT

Pharmaceutical compositions for the treatment of a decrease in the levels of protease activated receptor (PAR) mRNA caused by a lack or decrease of oxygen level and/or a lack or decrease of blood flow including pharmaceutically acceptable carriers and activators of PAR are provided. Methods for prevention of a decrease in the levels of protease-activated receptor PAR mRNA caused by lack or decrease in the oxygen level and/or lack or decrease in blood flow are also provided.

5 Claims, 7 Drawing Sheets

OTHER PUBLICATIONS

Peter J. Sabia, M.D., et al., "An Association Between Collateral Blood Flow and Myocardial Viability in Patients with Recent Myocardial Infarction," *The New England Journal of Medicine*, vol. 327, pp. 1825–1831, Dec. 1992.

Shigetake Sasayama, MD., et al., "Recent Insights Into Coronary Collateral Circulation," *Circulation*, vol. 85, No. 3, Mar. 1992.

Michael S. Bernatowicz et al., "Development of Potent Thrombin Receptor Anatagonish Peptides," *Journal of Medicinal Chemistry*, vol. 39, No. 25, pp. 4879–4887, 1996.

Demir Baykal, MD, et al., "Role of the Thrombin Receptor In Restenosis and Atherosclerosis," *The American Journal of Cardiology*, vol. 75, Feb. 1995.

Rachel Bar–Shavit et al., "Thrombin Immobilized to Extracellular Matrix is a Potent Mitogen for Vascular Smooth Muscle Cells: Nonenzymatic Mode of Action," *Cell Regulation*, vol. 1, pp. 453–463, May 1990.

Kurt R. Stenmark, MD, et al., "Vascular Remodeling in Neonatal Pulmonary Hypertension," *Chest*, 93, Mar. 3, 1988.

\* cited by examiner

SEQUENCE LISTING

<160> NUMBER OF SEQ ID NOS: 13

<210> SEQ ID NO 1
<211> LENGTH: 14
<212> TYPE: PRT
<213> ORGANISM: Homo sapiens

<400> SEQUENCE: 1

Ser Phe Leu Leu Arg Asn Pro Asn Asp Lys Tyr Glu Pro Phe
 1               5                  10

<210> SEQ ID NO 2
<211> LENGTH: 13
<212> TYPE: PRT
<213> ORGANISM: Homo sapiens

<400> SEQUENCE: 2

Ser Phe Leu Leu Arg Asn Pro Asn Asp Lys Tyr Glu Pro
 1               5                  10

<210> SEQ ID NO 3
<211> LENGTH: 12
<212> TYPE: PRT
<213> ORGANISM: Homo sapiens

<400> SEQUENCE: 3

Ser Phe Leu Leu Arg Asn Pro Asn Asp Lys Tyr Glu
 1               5                  10

<210> SEQ ID NO 4
<211> LENGTH: 11
<212> TYPE: PRT
<213> ORGANISM: Homo sapiens

<400> SEQUENCE: 4

Ser Phe Leu Leu Arg Asn Pro Asn Asp Lys Tyr
 1               5                  10

<210> SEQ ID NO 5
<211> LENGTH: 10
<212> TYPE: PRT
<213> ORGANISM: Homo sapiens

<400> SEQUENCE: 5

Ser Phe Leu Leu Arg Asn Pro Asn Asp Lys
 1               5                  10

-continued

```
<210> SEQ ID NO 6
<211> LENGTH: 9
<212> TYPE: PRT
<213> ORGANISM: Homo sapiens

<400> SEQUENCE: 6

Ser Phe Leu Leu Arg Asn Pro Asn Asp
  1               5

<210> SEQ ID NO 7
<211> LENGTH: 8
<212> TYPE: PRT
<213> ORGANISM: Homo sapiens

<400> SEQUENCE: 7

Ser Phe Leu Leu Arg Asn Pro Asn
  1               5

<210> SEQ ID NO 8
<211> LENGTH: 7
<212> TYPE: PRT
<213> ORGANISM: Homo sapiens

<400> SEQUENCE: 8

Ser Phe Leu Leu Arg Asn Pro
  1               5

<210> SEQ ID NO 9
<211> LENGTH: 24
<212> TYPE: DNA
<213> ORGANISM: Homo sapiens

<400> SEQUENCE: 9
atgggatccg gaggctgact acaa                                          24

<210> SEQ ID NO 10
<211> LENGTH: 21
<212> TYPE: DNA
<213> ORGANISM: Homo sapiens

<400> SEQUENCE: 10
ctgaaggtga agggaatgt g                                              21

<210> SEQ ID NO 11
<211> LENGTH: 21
<212> TYPE: DNA
<213> ORGANISM: Homo sapiens

<400> SEQUENCE: 11
ggataaagtc ttgatgatct c                                             21

<210> SEQ ID NO 12
<211> LENGTH: 24
<212> TYPE: DNA
<213> ORGANISM: Homo sapiens

<400> SEQUENCE: 12
atggaattct gccaccttag atcc                                          24

<210> SEQ ID NO 13
<211> LENGTH: 6
<212> TYPE: PRT
<213> ORGANISM: Xenopus laevis
```

-continued

```
<400> SEQUENCE: 13

Thr Phe Arg Ile Phe Pro
 1               5
```

AGENTS FOR THE PREVENTION OF DAMAGES CAUSED BY STRESS CONDITIONS

FIELD OF THE INVENTION

The present invention concerns agents for prevention or decrease of damages caused by stress conditions, particularly ischemica and/or hypoxia and to pharmaceutical compositions comprising such agents.

BACKGROUND OF THE INVENTION

Hypoxia, defined as lack or decrease of oxygen levels and ischemia, defined as lack or decrease of a blood supply, are common medical disorders of the vascular network, which may be caused by various reasons including: lack of oxygen such as in cases of drowning or suffocation, narrowing of blood vessels due to depositions on their walls, blockage of blood vessels for example by blood clots, and damage to blood vessels which can interpret their integrity. Decline or cessation of the normal blood supply to a specific tissue causes damage, which if prolonged can be irreversible leading to massive cell death. Where ischemia is caused due to the narrowing of coronary blood vessels and decrease of the blood supply to the heart, it may lead ultimately to myocardial infarction, one of the most common causes of mortality in the western world (Sabia, et al., *N. Engl. J. Med.*, 327:1825–1831, (1992); Sasayama, S., Fujita, M., *Circulation*, 85:1197–1204, (1992)).

The myocardial vascular network is regulated to a great extent by microenvironmental induced hypoxia caused by decrease of blood flow, i.e. ischemia. The molecular mechanism of hypoxia-regulated gene expression of cell surface receptors, involved in the regulation and maintenance of the cardiovascular system, is poorly understood. Insufficient blood supply following restenosis is the leading cause of heart failure as a result of ischemic stress.

Hypoxia has been suggested as one of the microenvironmental factors that induce angiogenesis (Schaper, et al., *Cir. Res.*, 28:671–679 (1971)) and modulate the phenotype of smooth muscle cells (Rugh, K. et al., *Cardiovac. Res.*, 21:730–736 (1987); Shweiki, et al., *Nature*, 359:843–845 (1992)) and myocytes (Stenmark, et al., *Chest.*, 93:127–133 (1988)). Hypoxic and ischemic stress causes a series of well documented changes in myocardial cells and tissues, including increased anaerobic glycolysis, loss of contractility and eventually cell death. In the heart, the induction of the proto-oncogenes fos and jun in cardiac myocytes exposed to severe hypoxia has been described (Konziolka, et al., *J. Neuroser.*, 69:494–499 (1988)). This induction occurred after exposure of between 1 and 4 hours to hypoxia, and then declined, coinciding with loss of myocytes contractility but prior to irreversible cell damage.

Current attempts to treat or prevent myocardial damage due to hypoxia or ischemia involve the development of collateral circulation, an alternative source of blood supply to the myocardium, to provide adequate flow to the major epicardial branches of the coronary artery, which blood flow is prevented by failure of the original vessels. This may be achieved by the secretion of the angiogenic factor bFGF or the upregulation of VEGF under hypoxia. Thus, while cardiac myocytes undergo ischemia, collaterals may develop actively by growth, DNA replication and mitosis of endothelial and smooth muscle cell (SMC). Collateral development by heparin binding growth factors has the disadvantage that it may take a rather long period before collateral develops and functionality take over pre-existing blood vessels.

Thrombin is an agent having multiple effects on the cells of the vascular and circulation systems. In hemostasis thrombin has a central role as a serine protease that converts fibrinogen to fibrin which clots blood. Additional functions of thrombin are widespread and diverse and appear to involve cellular activations which are mediated through cellular thrombin receptor(s). For example, thrombin is the most potent activator of platelets; it is chemotactic for monocytes; it is mitogenic for lymphocytes and mesenchymal cells including vascular smooth muscle cells and; it promotes numerous responses within the vascular endothelium. (Coughlin, et al., *J. Clin. Invest.* 89:351–355 (1992)). Because these cell activating functions of thrombin occur within the range of concentrations normally required for the clotting of blood, thrombin has been proposed to play important physiological roles not only in hemostasis and thrmobosis but may also have principle roles in mediating responses to vascular injury such as leukocyte chemotaxis (to mediate inflammation), cellular proliferation (to mediate restenosis), glomerulonephritis, wound repair (such as occurs in bone remodelling), smooth muscle cell proliferation and ligation of $\alpha_v\beta_3$ integrin through a cryptic yet functional RGD site (Bar-Shavit, et al., *J. Clin. Invest.*, 84:1096–1104 (1989); Bar-Shavit et al., *Cell Reg.*, 1:453–463, (1990)).

The cellular receptor of thrombin (ThR) is preferentially upregulated in advanced atherosclerotic lesions following percutaneous transluminal coronary angioplasty. This receptor is present also in rate ventricular myocytes implicated in the physiological maintenance of these cells.

Thrombin receptor is a seven transmembrane G-coupled protein that belongs to a new family of receptors termed "*Protease Activated Receptors*" (PAR). Unlike most growth factor receptors, the activation of PAR does not require the traditional ligand receptor complex formation. Instead, receptors of this family serve as substrates for protease digestion to yield an irreversible form of activated receptor that conveys further cellular effects. Activation of the ThR was found to be important in various physiological systems such as myocytes (Glenbotski et al., *J. Biol. Chem.*, 268:20646–20652 (1993)), keratinocytes (Santulli et al., *PNAS*, 92:1–6 (1995)) and astrocyte proliferation (Grabham, P. and Cunningham, D., *J. Neurochem.*, 64(2):583–591 (1995)). Other PARs have been discovered to have importance in diverse physiological systems (Coughlin et al., *PNAS*, 91; 9200–12, (1994)) an example being PAR-2 receptor which is involved in the inflammation cascade systems (Nystedt et al., *PNAS*, 91:9208–9212 (1994); Nystedt et al., *Eur. J. Biochem.*, 232:84–89 (1995); Nystedt et al., *J. Biol. Chem.*, 271:19910–19915 (1996); Schmidt, *J. Biol. Chem.*, 271:9307–9212 (1996)).

SUMMARY OF THE INVENTION

The present invention is based on the surprising finding that mRNA levels of the thrombin receptor, a member of the Protease-Activated Receptor (PAR) family, decrease under conditions of stress, such as hypoxia. It has further been found that activating the ThR prior to or during the exposure to hypoxia, prevents said hypoxia-induced decreased in the level of mRNA. Administration of a ThR activating agents to cells under normal conditions, i.e. normal oxygen level, did not cause an increase in the normal levels of ThR mRNA levels.

ThR is a growth promoting receptor for cells of different origins, for example: fibroblasts, smooth muscle cells, astrocytes, etc. In myocytes activation of ThR induces hypertrophy and increases atrial natriuretic factor gene expression.

Therefore, maintaining a normal level of ThR mRNA is necessary for the well being and maintenance of cells in general and of myocytes in particular. Thus a decrease in the level of ThR mRNA under stress conditions, such as hypoxia contributes to the deterioration of cells, and particularly myocytes under these conditions. Agents capable of preventing such a stress-induced decrease in the level of ThR mRNA may help prevent or decrease some of the damages caused to the cells under stress conditions.

Thus, the present invention provides an agent for preventing the decrease in the levels of protease-activated receptor (PAR) mRNA under stress conditions, said agent being an activator of the PAR.

The term "preventing the decrease of mRNA levels" refers to a complete prevention of the decrease of these levels and reversal to normal mRNA levels featured by the same type of cells under normal conditions. Alternatively, this term refers to situations where there is partial prevention, i.e. while the mRNA level of the PAR in the cells which are under the stress condition treated by the activator of PAR, may not reach the level featured in those cells under normal (i.e. non-stress) conditions, it nevertheless is higher than corresponding mRNA levels of PAR in cells exposed to the same stress conditions and which are not treated by the activator of PAR.

The term "Protease-Activated Receptor" (PAR) refers to a family of G-protein coupled seven transmembranal receptors which are activated by proteolytic cleavage of their extracellular amino terminus. Examples of such PAR are the thrombin receptor, (Vu et al., *Cell*, 64:1057–1068 (1991)); and PAR-2; (Santulli et al., *Cell Biol.*, 92:1–5, 1995)).

The term "activators" refers to agents which are capable of causing an interaction of the PAR to the G-protein, for example, as determined by initiation of cell signaling. Cell signaling can be determined, for example, in the same manner as shown for the activation of the src family kinased, wherein Pertussis Toxin, a G-protein inhibitor, partially inhibits src-like kinase. Other modes of determining activation of G-protein seven transmembrane receptors are well known in the art. The mechanism of activation may be by cleavage of the extracellular amino terminus of the PAR receptor.

Examples of suitable activators which work by cleavage of the PAR are various proteases particularly serine proteases such as non-physiological trypsin, catepsin G, plasmin, etc. An example of a protease specifically suitable for ThR is either the native thrombin or α-thrombin.

Alternatively, the activation can be achieved by providing analogues of the receptor cleavage products, i.e. the internal ligand (also termed "tethered receptor") which are able to mimic a cleaved receptor and thus activate it. For example, thrombin receptor activating peptides (TRAP) are capable of mimicking the activated receptor by activating directly the second transmembrane-loop of the receptor, thereby by creating tethered ligand and cellular response.

Other activators of various PARs which work by mimicking the tethered receptor are well known in the art.

For ThR various peptides termed *"Thrombin Receptor Activating Peptides"* (TRAP) are used. Examples of TRAP are peptides selected from the following group:

-SFLLRNPNDKYEPF (SEQ ID NO: 1),
-SFLLRNPNDKYEP (SEQ ID NO: 2);
-SFLLRNPNDKYE (SEQ ID NO: 3);
-SFLLRNPNDKY (SEQ ID NO: 4);
-SFLLRNPNDK (SEQ ID NO: 5);
-SFLLRNPND (SEQ ID NO: 6);
-SFLLRNPN (SEQ ID NO: 7); and
-SFLLRNP (SEQ ID NO: 8).

Another type of activator acting as an analog of the cleavage product of a ThR isolated from *Xenopus laevis* is the peptide TFRIFP (SEQ ID NO: 13).

The murine protease activated receptor PAR-2 is activated by the peptide SLIGRL.

The term "stress conditions" refers to conditions which are substantially different from normal or optimal conditions necessary for maintenance or growth of cells, tissue or organs without being so extreme so as to be immediately lethal, although exposure to such conditions for a prolonged period of time may eventually lead to massive cell-death. Examples of such stress conditions are: hypoxia, ischemia and hypoglycemia. Preferably, the stress conditions are hypoxia and/or ischemia which are connected. As explained above, ischemia actually leads eventually to hypoxia, since the tissue or organ is deprived of oxygen carrying blood.

The agent of the present invention may serve as an active ingredient in a pharmaceutical composition which purpose is to prevent or diminish damages to the cells, tissues or organs caused by stress conditions as specified above, in particular hypoxia and/or ischemia.

By a preferred embodiment the pharmaceutical composition is intended to prevent or diminish damage caused by stress conditions, due to decrease in the level of ThR mRNA, since normal levels of ThR mRNA are necessary for the maintenance of many cell types, notably myocytes.

Therefore the present invention further concerns a pharmaceutical composition for the treatment of cardial disorders caused by lack of oxygen or blood flow comprising a pharmaceutically acceptable carrier and as an active ingredient a therapeutically effective amount of an active agent according to the description as specified above.

Examples of such disorders are delayed ischemic heart failure, myocardial infarction, complete occlusion and angina pectoris.

The term "treatment" in the context of the present invention does not necessarily mean complete recovery but can also refer to a certain amount of prevention, or alleviation of some of the damages caused by the stress conditions, which preferably are hypoxia and/or ischemia.

Preferably, the cardial disorders are myocardial disorders.

Since not all the damage caused by hypoxia/ischemia is due to decrease of the level of ThR mRNA, but also to other mechanisms, the pharmaceutical composition of the invention should preferably be administered together with other agents or medicaments capable of minimizing damage caused to the cardial system by stress conditions.

The activation of a thrombin receptor has a variety of affects on the blood, vascular system, smooth muscle cells, etc., not all of which are beneficial. Therefore, it is preferable as much as possible to administer the ThR activator to the desired site directly and not systematically. Thus, in accordance with the preferred embodiment of the present invention the pharmaceutical compositions are administered directly to the heart, for example, by local reperfusion to the heart or by administering locally to the heart compounds capable of low and controlled release of the pharmaceutical composition.

Since the purpose of the pharmaceutical composition of the invention is to prevent or decrease cardial, especially myocardial damage caused by hypoxia and/or ischemia, it should be administered as close as possible to the initiation of the hypoxia and/or ischemic conditions.

The present invention will now be further illustrated with reference to some non-limiting examples.

DETAILED DESCRIPTION OF THE INVENTION

I. Experimental Procedure

Figure 1:
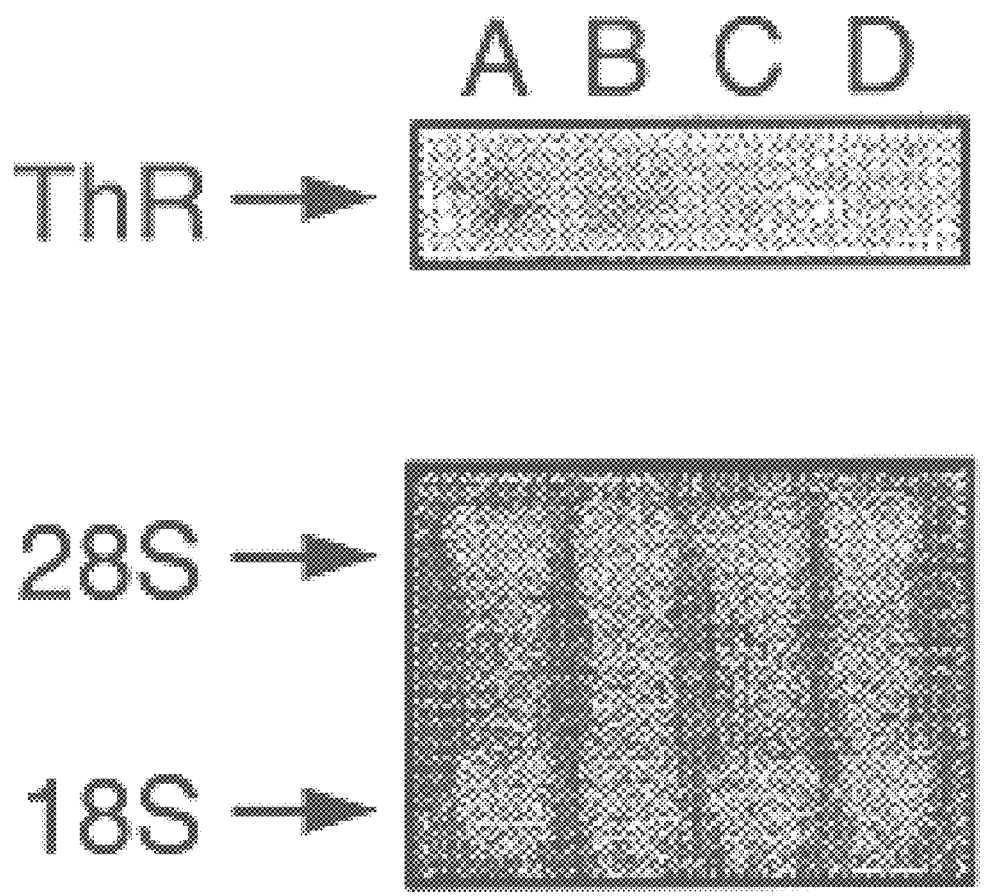
FIG. 1 shows northern blot of total RNA isolated from either normal pigs hearts (lanes A and D) or ischemic pigs hearts (B,C and E,F) and determined for the level of ThR (lanes A–C) or L-19 (lanes D–F)

RNA Isolation and Northern blot analysis:

RNA was prepared using TRI-Reagent (Molecular Research Center, Inc. Cincinnati) according to the manufacturer's instructions. The RNA (20 μg of total RNA) was separated by electrophoresis through a 1.1% agarose gel containing 2 M formaldehyde, transferred to a nylon membrane (Hybond N; Amersham) and hybridized either to cDNA probes or PCR product radiolabeled by random primer extension with [α-$^{32}$P]dCTP (Koch, C. J., *Exp. Med. Biol.*, 157:123–144 (1982)) for 24 hours at 42° C. For the detection of ThR a 250 nucleotide PCR product was used. The membrane was washed twice for 30 mins. at room temperature with 1×SSC containing 0.1% SDS and twice for 30 mins. at 55° C. with 0.1×SSC, containing 0.1% SDS. The blots were exposed for 2–4 days at −70° C. and the relative amounts of mRNA transcripts were analyzed by laser densitometry using an Ultrascan XL Enhanced Laser Densitometer and normalized relative to an internal β-actin controls.

Reverse transcriptase (RT)-PCR:

1 μg of total RNA extracted as described above, was taken for the reverse transcription reaction, using MuMLV Reverse Transcriptase (Gibco BRL) and Oligo (dT) 15 primer (Promega; Madison, Wis.). Subsequent amplification of the resultant first strand cDNA using Taq polymerase (Promega; Madison, Wis.) in a GeneAmp PCR system (Minicycler, M J Research) thermal cycler, was performed according to established procedures (Coleman, N C, *J. Natl. Cancer Inst.*, 80:310–317 (1988)). The primers used were selected from data derived from GenBank, as follows:

ThR primers: 5' ATGGAATTCTGCCACCTTAGATCC (SEQ ID NO: 12)

5' ATGGGATCCGGAGGCTGACTACAA (SEQ ID NO: 9)

L19 primers: 5' CTGAAGGTGAAGGGGAATGTG (SEQ ID NO: 10)

5' GGATAAAGTCTTGATGATCTC (SEQ ID NO: 11)

Thirty-seven cycles of amplification were performed, each consisting of denaturation at 94° C. for 30 seconds (sec), reannealing at 55° C. for 30 sec, and extension at 72° C. for 1 min. The PCR product was analyzed on a 1% Tris-borate/EDTA agarose gel. Based on the known number of base pairs between the specific sense and antisense primers used for amplification, the size of the human ThR is predicted at 250 bp and of L19 is of 350 bp.

Cells:

NIH3T3 murine fibroblasts; NIH3T3 were grown in Dulbecco's modified Eagle medium (DMEM) containing 10% calf serum.

LDH activity:

Cell viability under hypoxia conditions was measured by lactate dehydrogenase (LDH) assay of the medium by using diagnostic kit according to the manufacturer's instructions (Sigma, St. Louis, Mo.). Released LDH is a stable enzymatic marker that correlates with cell viability. Total LDH activity was determined in culture medium plus LDH released from the cells after treatment with 0.5% Triton X-100. All results are expressed as mean±SEM of triplicate sample (I—Weiscner, M S et al., 1998. Induction of endothelial cell PAS domain protein-1 by hypoxia: characterization and comparison with hypoxia-inducible factor-1-alpha. *Blood*, 92(7);2260–8. II—Brooks et al., 1998. Modulation of VEGF production by pH and glucose in retinal muller cells. *Curr. Eye Res.*, 17(9):875–882).

Hybridization probes:

A full length mouse trombin receptor cDNA fragment of 2 kb cloned onto the EcoRI sites of pBluescript plasmid GLUT 1 cDNA fragment of 1.9 kb in size, cloned from a rat brain cDNA library (E. Keshet, Department of Molecular Biology, Hebrew University Medical School). As a house keeping control gene α-actin was used. cDNA fragments labeled with $^{32}$P by randomly primed DNA synthesis were used.

EXAMPLE 1

Effect of Ischemia ThR mRNA Levels Under Ischemia in Pig Heart

Sections of the relevant heart regions (either ischemic or normal) were obtained from 4 domestic pigs of either sex weighing 15 to 30 kg. Myocardial ischemia in pig hearts was induced by, reocclusion for 3, 5 and 7 mins. each occlusion being followed by 20 min. reperfusion. Thereafter repeated occlusions of 10 min. each were performed followed by 20 min. reperfusion for a total period of 6 hrs. Hearts with TRAP are retrieved after 6 hrs. of intermittent ischemia. In parallel the same treatment is performed except for the perfusion with TRAP for ThR activation and instead the hearts were perfused with saline. Both section and total RNA were extracted from normal and ischemic zones of the heart and were processed for RNA hybridization analysis. The methodology involved included: isolation of RNA from tissues, RT-PCR and Northern blot analysis.

The results are shown in FIG. 1. As can be seen ischemic hearts (lane B,C) showed a decrease in ThR mRNA levels as compared to normal hearts (lane A). No corresponding decrease was evident in the mRNA of a housekeeping gene L-19 (lanes D–F).

EXAMPLE 2

Prevention of Decrease of ThR mRNA Levels Under Hypoxia by ThR Activators

Figure 2:
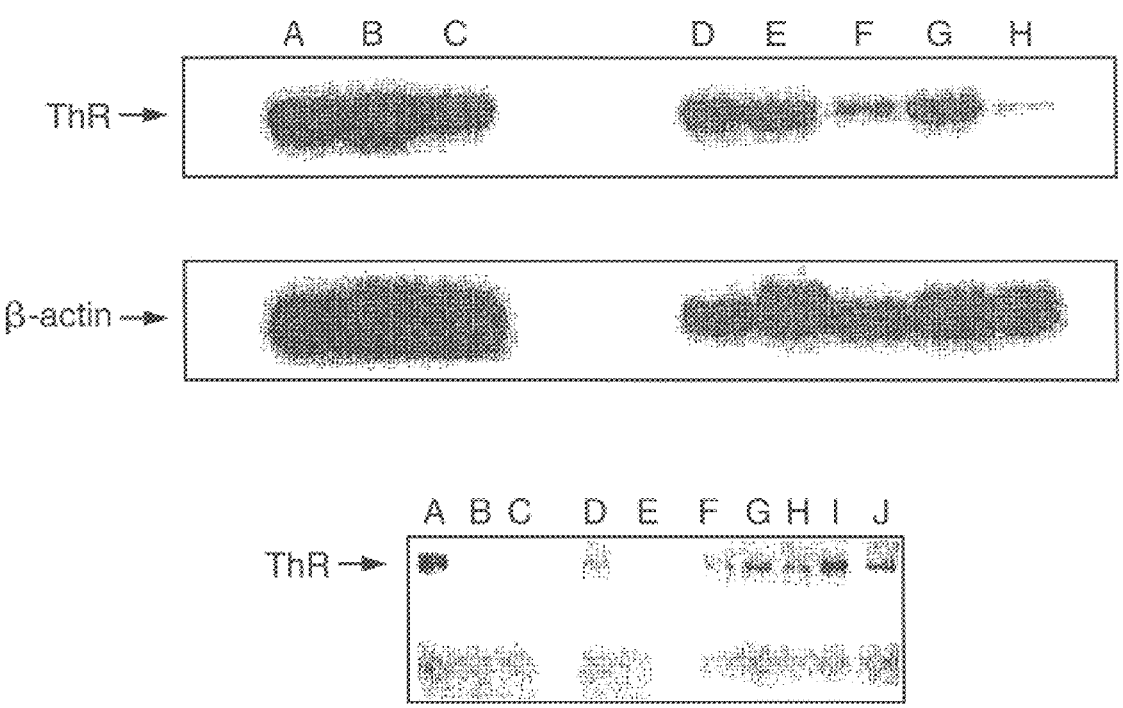
FIG. 2 shows northern blot of total RNA isolated from either normal rat ventricular myocytes (lanes A–C) or cell cultures subjected to hypoxia (lanes D–H) in the presence (lanes C,E and G) or absence (lanes A,B,D,F,H) of α-thrombin. Myocytes were subjected to 3 hours (lanes G and H), 2 hours (lane F) or 1 hour (lane D and E) hypoxia.

Primary cultures of neonatal rat ventricular mycocytes were subjected to hypoxia conditions (0% oxygen, 20 torr), and the level of ThR transcripts were compared to the level of the receptor transcripts in cells under normal oxygen levels (21% oxygen). As shown in FIG. 2, ThR mRNA levels declines in a time dependent manner, with complete disappearance following 4 hour hypoxia (FIG. 2; lanes B,C). This effect was reversible, since cells subjected to 4 hours hypoxia that were exposed against to normal oxygen levels (21% oxygen) for 18 hours, regained the normal ThR transcript levels (data not shown). The 4.1 kb mRNA was detected following hybridization with full length ThR cDNA and the intensity of the bands was quantitated by densitometry and normalized to the actin transcript levels. Thus, it is event that ThR transcript disappears under hypoxia conditions, a situation that can be reversed by reverting to normal oxygen tension.

Figure 3:
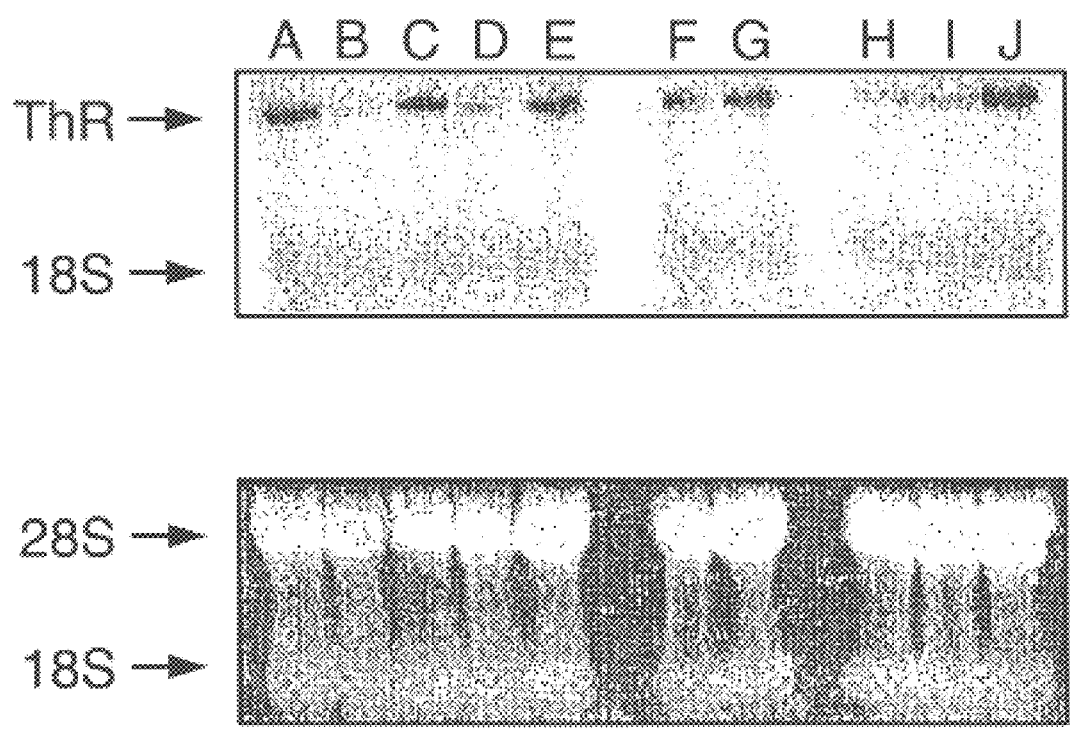
FIG. 3 shows northern blot of total RNA isolated from rat ventricular myocytes subjected to 4 hours hypoxia (lanes B,C, E, G,H and J), or under normal conditions (A,D,F and I) either in the absence (lanes B,C, E) or presence of 1 μM TRAP (lanes G, H) or 20 μM TRAP (lane J). Some of the normal myocytes (lanes A,D,F and I) were also incubated with either 1 μM TRAP (lane F) or 20 μM TRAP (lane I). An irrelevant ligand (i.e. bFGF, 100 nM) was added to normal (lane D) or hypoxia treated cells (lane E)

The level of ThR mRNA following hypoxia, in the presence of α-thrombin was also determined. For this, rat ventricular myocytes were subjected to serum free conditions and α-thrombin ($5 \times 10^{-8}$M) was added for a period of 48 hours and the level of ThR was determined. The results are shown in FIG. 3. While under normal conditions the presence of α-thrombin did not affect significantly the level of ThR mRNA (FIG. 3, lanes A–C), a full protection i.e. prevention of decrease of ThR mRNA levels following 2 hours hypoxia was obtained, in the presence of α-thrombin (FIG. 2, lane G and H). As already mentioned above, ThR transcript level completely disappeared following 3 hours hypoxia, partially disappearance following a 2 hour hypoxia (FIG. 2, lane H) and no effect was seen when cells were subjected to 1 hour hypoxia (FIG. 3, lanes D and F), as compared to the level of mRNA of β-actin which is a housekeeping gene.

From the above results, it is evident that ThR mRNA decreased under hypoxia, and this hypoxia-depended decrease could be prevented if the cells were treated prior or during the exposure to hypoxia with an activator of ThR such as α-thrombin.

The protecting effect was not specific only to primary cultures of neonatal rat ventricular myocytes but was also observed when NIH3T3 fibroblasts were subjected to hypoxia following prior treatment by TRAP. No induction of ThR mRNA expression was observed under normal conditions (i.e. non-stressed conditions) following addition of TRAP, as compared to the level of expression of normal ThR transcripts present under non-hypoxic conditions (data not shown).

NIH3T3 cells subjected to hypoxia show reduction in the levels of ThR mRNA. However, the level of ThR mRNA in NIH3T3 cells transfected with Ras or Src oncogenes remained unaltered even under hypoxia as compared to such transfected cells present under normal conditions. Transfected NIH3T3 cells either with Ras or Src were thus shown to be non effected by the stressed hypoxic conditions (data not shown).

Thus it can be concluded that when the signaling cascade is "turned on", as part of ThR cascade of events (for example in expression of Ras or Src), the level of ThR mRNA is protected under hypoxia.

Vav oncogene could potentially serve as a linker between tyrosine kinase signaling pathway of activated receptors and G-protein family. This can be mediated by specific interactions either with various adapter/proteins or through a GDP/GTP exchange factor. Vav is part of ThR activation pathway as demonstrated via the phosphorylation of the 95 kDa vav protein following either α-thrombin or TRAP stimulation. NIH3T3 mouse fibroblast cells transfected either with proto-vav oncogene (i.e. K62 cell line, transfected with proto-vav inserted into a mammalian expression vector pSK115), a mutant version of vav oncogene, R695L, in which Arginin R695 of vav-SH2 domain was substituted for Leucine (32), or a mutant defective in SH3 domain of vav, (P832L) were used in the experimental system. The vav oncogene mutants failed to show any phosphorylation, following activation with TRAP, as compared to proto-vav induced phosphorylation of the vav protein, although the level of the protein was not altered (data not shown).

These results demonstrate that cells transfected with the vav oncogene also remained unaltered under hypoxic conditions. This was shown true for either transfected proto vav oncogene or the SH2 or SH3 mutants of the oncogene. The level of ThR transcripts were compared to non transfected NIH3T3 cells and mock transfected. Hypoxic conditions were monitored by GLUT-1 expression as compared to the RNA levels applied.

EXAMPLE 3

Effect of PKC Inhibitor on Levels of ThR Transcripts Under Hypoxia

Activation of ThR initiates cell signaling cascades involving the G-protein system, PKC activation and members of the typrosine kinase family such as src and MAP kinase downstream. The fact that activated receptors are protected, suggests that initiation of cell signaling relays a message that ultimately leads to the protection of ThR from decaying under hypoxia conditions. Therefore the effect of interruption of the signaling cascase on the protection effect was analyzed. For this, calphostin C, a protein kinase C (PKC) inhibitor was added during the activation of ThR with TRAP. The results are shown in FIG. 4.

Figure 4A:
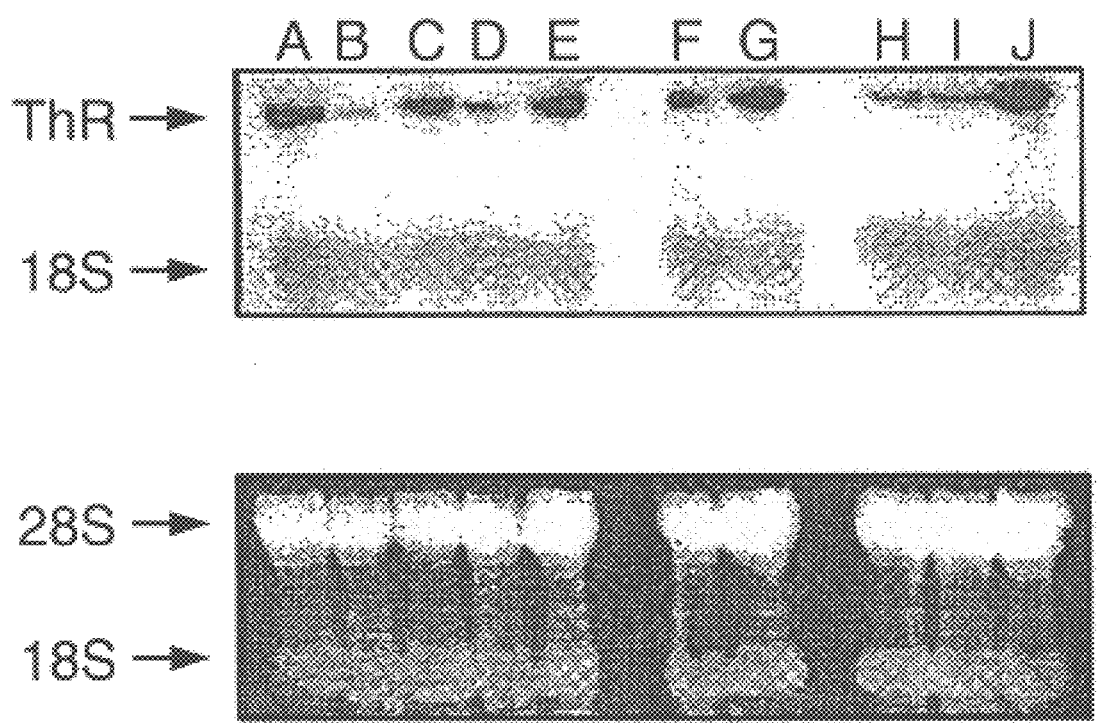
FIG. 4A shows northern blot analysis of RNA isolated from the myocytes. TRAP at a concentration of 1 μM was added (lanes F–J) to serum free myocytes, subjected to hypoxia (lanes E, G and I). The level of ThR mRNA was compared to normal (lanes A and J) and hypoxic conditions (lanes B,C). Calphostin C either at 1 nM (lanes F and G) or 100 nM (lanes H–J) was added to the cells prior to the addition of TRAP. Calphostin C at a concentration of 200 nM did not affect the level of ThR mRNA under normal conditions. The blots were probed with $^{32}$P-labeled full length rat ThR cDNA and $^{32}$P-α-actin. Laser densitometry was used to quantitate the intensity of the bands relative to control bands of α-actin.
Figure 4B:
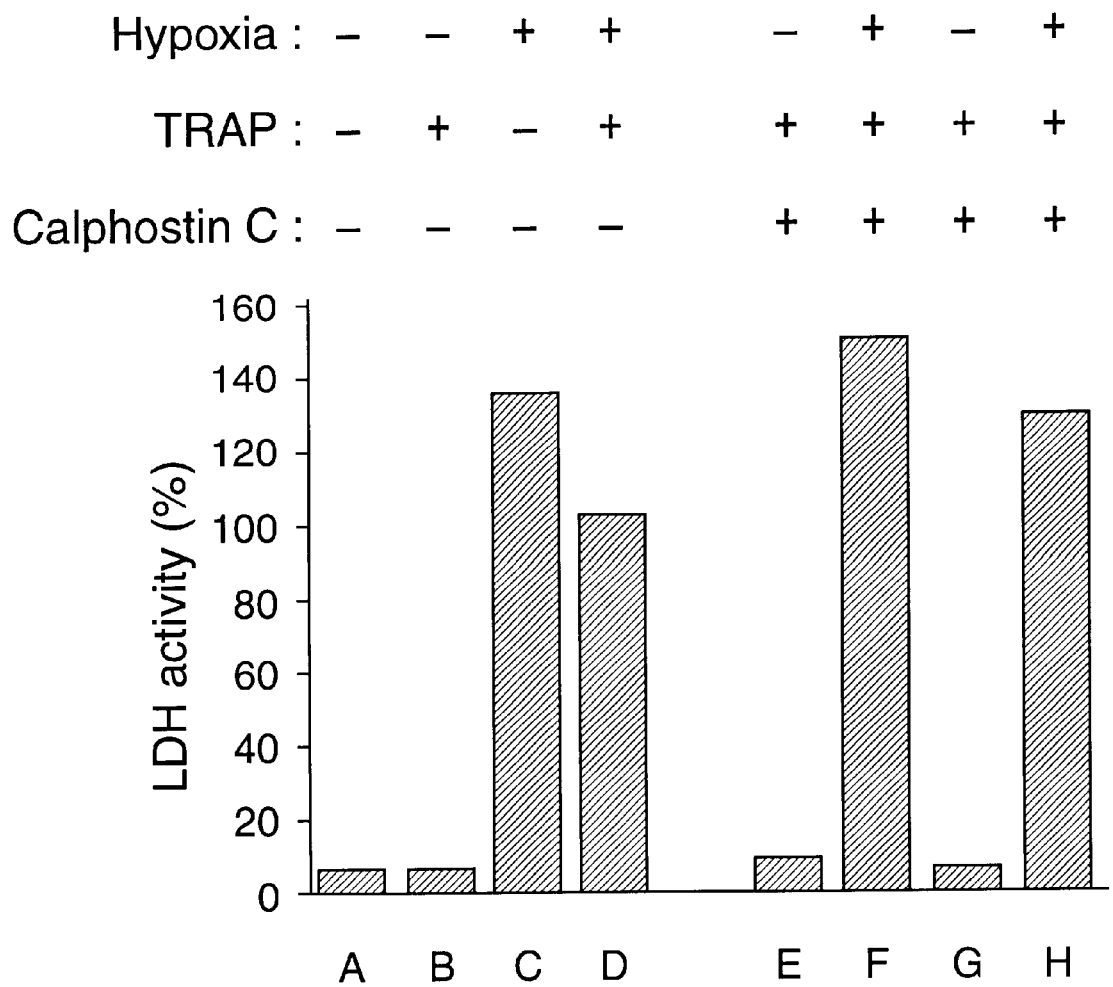
FIG. 4B. LDH levels were measured in the medium of normal (A,B,E,G) and hypoxic (C,D,F,H) myocytes. TRAP (10 μM) was added (for 48 h) to normal cells (B,E,G) or prior to subjecting the cells to hypoxia (D,F,H). Cells were treated with calphostin C at 10 nM (E,F) or 100 nM (G,H). LDH levels were determined at 340 nm.

Both calphostin C (1 nM and 100 nM) and TRAP added under normal conditions did not affect the level of ThR transcripts (FIG. 4, lanes F & H) neither did calphostin C (i.e. 100 nM) alone (FIG. 4, lane J). TRAP activated ThR in the presence of calphostin C, showed no longer the protection under hypoxia (FIG. 4, lanes G and I), the loss of the protection in the presence of calphostin C, was not observed when TRAP alone was present under hypoxia (FIG. 4, lane E) as compared to normal conditions (FIG. 4, lanes A & D) or hypoxic one (FIG. 4, lanes B & C). The interruption in ThR protected transcript levels in the presence of calphostin C, was specific and did not result from changes in RNA levels (FIG. 4, lower section). Likewise, the addition of calphostin C in the presence and absence of TRAP did not affect the stressed hypoxic conditions as observed by the released LDH activity (FIG. 4B, lower section).

EXAMPLE 4

Regulation of Glut-1

Figure 5:
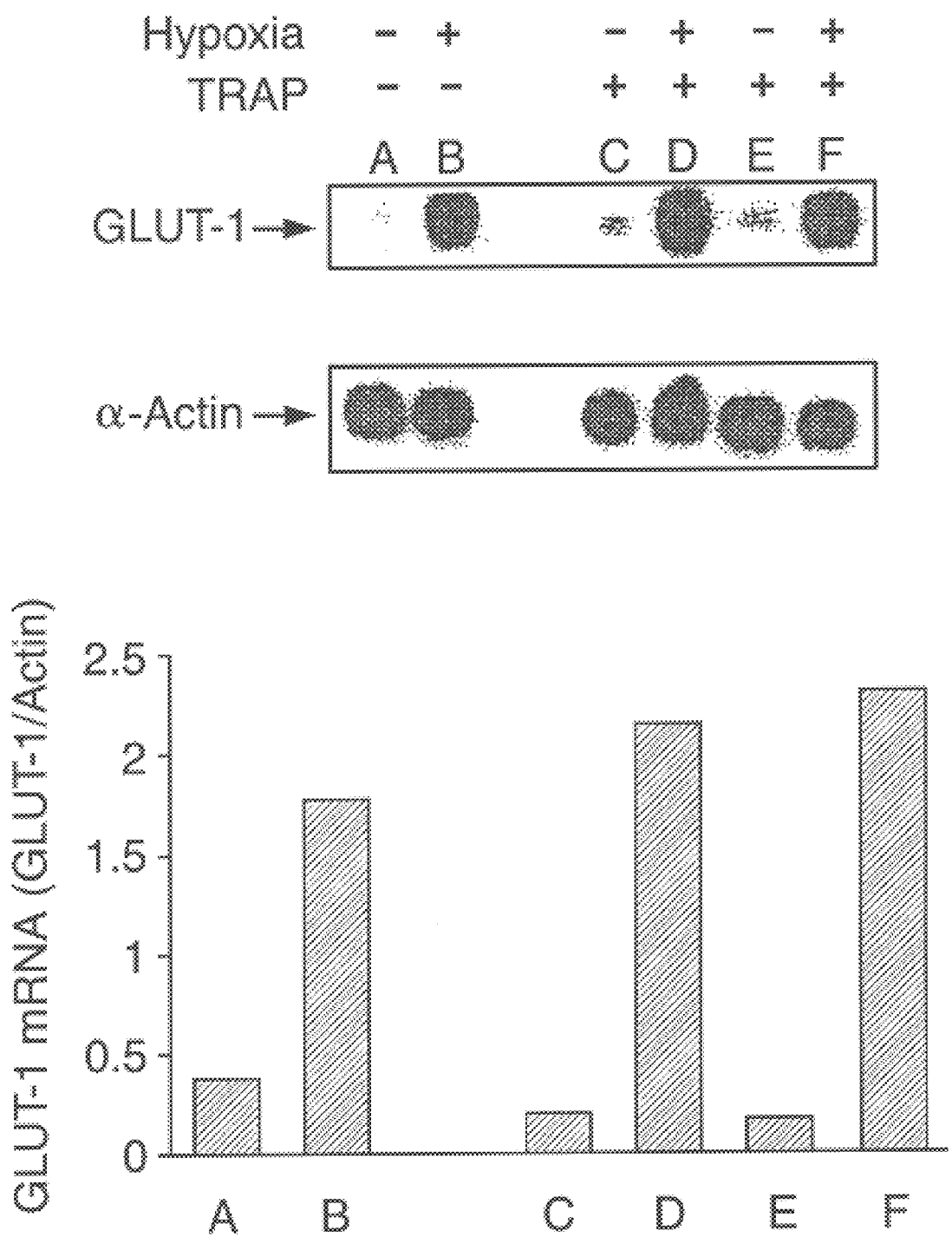
FIG. 5 shows northern blot analysis of Glut-1 in NIH 3T3 under normal (A,C,E) and hypoxic (B,D,F) conditions. TRAP activation at 1 μM (for 48 h) (C,D) or 20 μM (E,F). The blots were probed with $^{32}$P-labeled Glut-1 cDNA and $^{32}$P-α-actin (II). Lower section. Laser densitometry was used to quantitate the intensity of the bands relative to control bands of α-actin.
Figure 6:
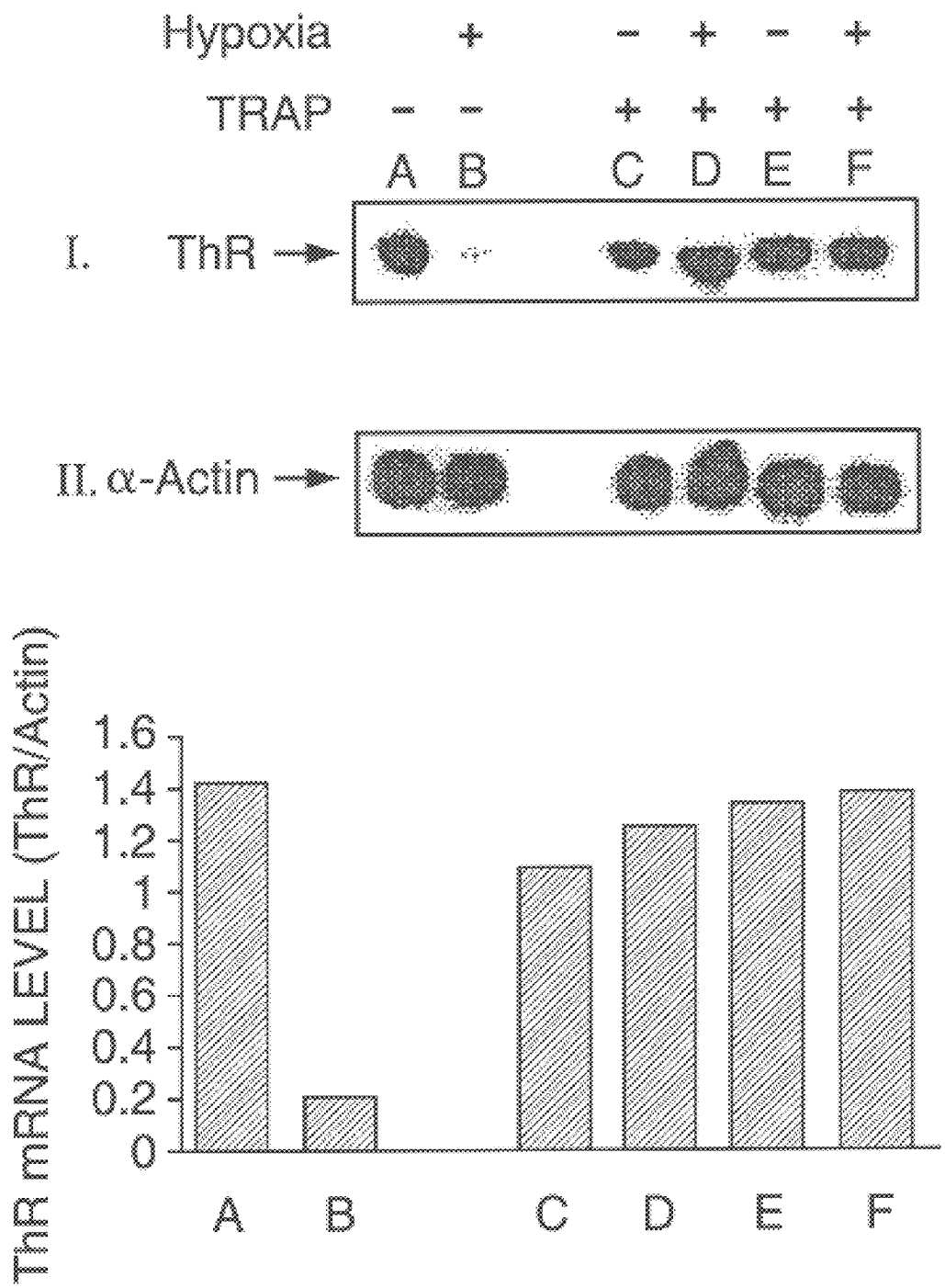
FIG. 6 shows northern blot analysis of mRNA. The level of ThR was determined either normal (A,C,E) and or hypoxic conditions (lanes B,D,F). NIH3T3 fibroblast cells were either activated via addition of 1 μM TRAP (C,D), 20 μM TRAP (E,F) or non treated (A,B). The blots were probed with $^{32}$P-labeled full length rat ThR cDNA and $^{32}$P-α-actin.

Activation of ThR did not affect the hypoxic condition as was observed by the induced levels GLUT-1 transcript, a GRP that has been characterized as a glucose transporter and known to be upregulated under hypoxia (FIG. 5, lanes B, D & F). The protection effect was not specific only to primary cultures of neonatal rat ventricular myocytes but was also observed when NIH3T3 fibroblasts were subjected to hypoxia following prior treatment of TRAP (FIG. 6, lanes D & F, 1 $\mu$M or 20 $\mu$M respectively). No induction of ThR mRNA was observed under normal conditions following addition of TRAP (FIG. 6, lanes C & E, 1 $\mu$M or 20 $\mu$M, respectively) as compared to normal ThR transcript level (FIG. 6, Lane) or hypoxic conditions (FIG. 6, lane B). The protection in ThR mRNA level is specific since no induction in $\alpha$-actin level (a house keeping control gene) was observed (FIGS. 5 & 6, lower section).

What is claimed is:

1. A method to prevent a decrease in the levels of protease-activated receptor (PAR) mRNA caused by lack or decrease in the oxygen level and/or lack or decrease in blood flow for the treatment of a cardial disorder selected from the group consisting of ischemic heart failure, myocardial infarction, complete occlusion and angina pectoris, comprising:

administering to a subject in need of such treatment effective amount of an agent, wherein the agent is an activator of PAR.

2. A method according to claim 1, wherein the protease activated receptor is Thrombin Receptor (ThR).

3. A method according to claim 2, wherein the agent is α-thrombin.

4. A method according to claim 2, wherein the agent is a Thrombin Receptor Activating Peptide (TRAP).

5. A method according to claim 4, wherein the agent is a TRAP comprising a sequence selected from the following group:

-SFLLRNPNDKYEPF (SEQ ID NO: 1);

-SFLLRNPNDKYEP (SEQ ID NO: 2);

-SFLLRNPNDKYE (SEQ ID NO: 3);

-SFLLRNPNDKY (SEQ ID NO: 4);

-SFLLRNPNDK (SEQ ID NO: 5);

-SFLLRNPND (SEQ ID NO: 6);

-SFLLRNPN (SEQ ID NO: 7); and

-SFLLRNP (SEQ ID NO: 8).

* * * * *